United States Patent [19]

Hernestam et al.

[11] 4,235,875
[45] Nov. 25, 1980

[54] ANTICARIES PIPERIDINO COMPOUNDS

[75] Inventors: Sven E. H. Hernestam, Malmo; Lars O. Willard, Hollviksnas; Aina L. Abramo; Hans-Bertil Johansson, both of Malmo, all of Sweden

[73] Assignee: A.B. Ferrosan, Malmo, Sweden

[21] Appl. No.: 899,598

[22] Filed: Apr. 24, 1978

Related U.S. Application Data

[63] Continuation-in-part of Ser. No. 678,960, Apr. 21, 1976, abandoned.

[30] Foreign Application Priority Data

Apr. 22, 1975 [GB] United Kingdom ............... 16673/75

[51] Int. Cl.³ ..................... A61K 7/22; C07D 211/14
[52] U.S. Cl. .................................. 424/54; 260/345.1; 260/456 R; 546/184; 546/243; 546/246; 546/248; 562/590; 568/853
[58] Field of Search ...................... 424/54; 260/293.9; 546/248

[56] References Cited

U.S. PATENT DOCUMENTS

| | | | |
|---|---|---|---|
| 2,921,886 | 1/1960 | Panepinto | 424/54 |
| 3,322,618 | 5/1967 | Taylor | 424/263 |
| 3,446,808 | 5/1969 | Cyba | 260/293.9 |
| 4,144,320 | 3/1979 | Hernestam et al. | 424/54 X |

OTHER PUBLICATIONS

Clark et al., *The Encyclopedia of Chemistry*, Reinhold Pub. Co., New York, 1957, pp. 683–684.
Weisgerber, D., Letter from Chemical Abstracts Service to G. W. Hueschen, 8/29/79.
Gilman, H. (Editor), Organic Chemistry, 2nd Edition, vol. I, John Wiley and Sons, New York, 1943, p. 20.
Morrison, R., et al., Organic Chemistry, 2nd Edition, Allyn and Bacon, Boston, 1966, pp. 137 and 1187.

*Primary Examiner*—Henry R. Jiles
*Assistant Examiner*—Richard A. Schwartz
*Attorney, Agent, or Firm*—Gordon W. Hueschen

[57] ABSTRACT

Novel alkyl 1-(hydroxyalkyl)piperidines and acid addition salts thereof, useful as inhibitors of dental plaque and therefore also useful against dental caries and periodontitis, are disclosed. Methods of making same, orally-acceptable compositions thereof, a method of treating therewith, and important and novel intermediates for the production thereof are also disclosed.

43 Claims, 3 Drawing Figures

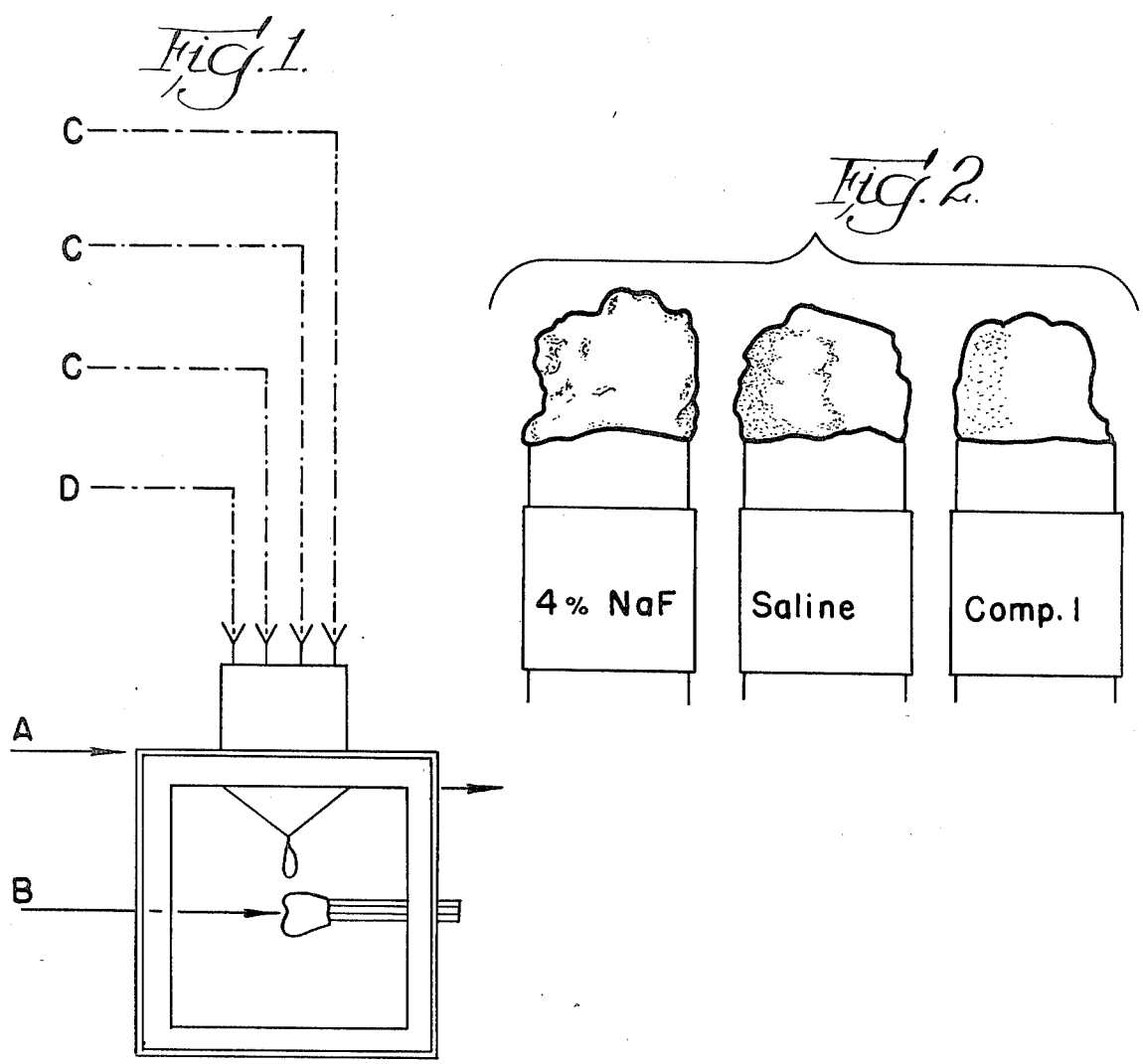
Fig. 1.
Fig. 2.
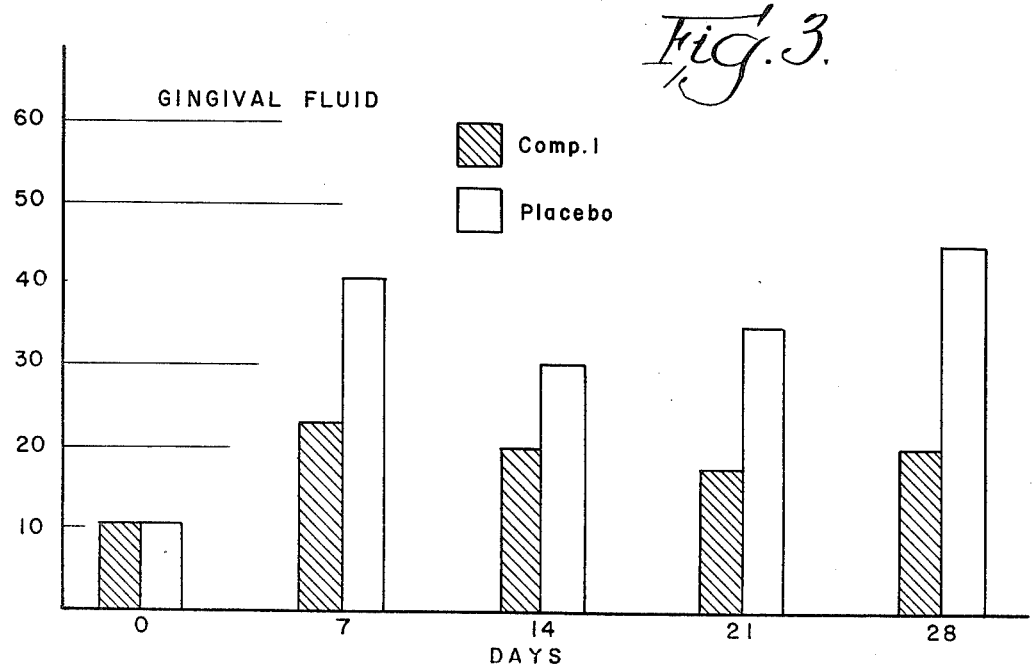
Fig. 3.

ANTICARIES PIPERIDINO COMPOUNDS

The present application is a continuation-in-part of our prior-filed copending application Ser. No. 678,960, filed Apr. 21, 1976, now abandoned.

BACKGROUND OF INVENTION

(1) Field of Invention

Alkyl 1-(hydroxyalkyl)piperidines and acid addition salts thereof; anti-plaque, anticaries and antiperiodontitis compounds; oral and dental hygiene compositions thereof, method of treating therewith, preparation thereof.

(2) Prior Art

The oral diseases periodontitis and dental caries are plaque-related problems of a complex nature and origin, which have until the present been most successfully treated or obviated by the mechanical removal of plaque, since the chemical approach to plaque inhibition has not been successful. The present invention, however, provides compounds of a special chemical structure without pronounced antibacterial effect and with low toxicity and which have been shown to be effective for the inhibition of dental plaque and, accordingly, also for the inhibition of dental caries and periodontitis, which problems or ailments are caused by undue buildup of dental plaque and resulting complications, all as more fully considered hereinafter under "PHARMACOLOGY".

All established more or less useful compounds of the prior art have been found to be characterized by serious shortcomings and/or side effects, and there exists a clear and ever-growing demand for more specific and advantageous compounds or treatments in this activity and utility area, especially for anti-plaque, anticaries, and anti-periodontitis products and methods. The fulfillment of this demand is one of the objects of the present invention, as will become more fully apparent hereinafter.

SUMMARY OF THE INVENTION

This invention relates to novel alkyl 1-(hydroxyalkyl)piperidines, acid addition salts thereof, orally-acceptable compositions containing the same, a method of using the same for their anti-plaque or anticaries properties, and a process for the manufacture thereof, as well as novel intermediates in the production thereof. The novel compounds provided by the present invention are selected from the group consisting of (a) alkyl 1-(hydroxyalkyl)piperidines having the General Formula I:

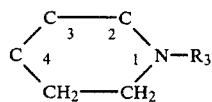
(I), which are gem-substituted in 2, 3, or 4 position with

wherein $R_1$ is an alkyl group, straight or branched, and $R_2$ is hydrogen or an alkyl group, straight or branched, $R_1$ and $R_2$ together having 3–14 carbon atoms, and wherein $R_3$ is an alkyl group, straight or branched, of 2–10 carbon atoms and substituted with a hydroxy group, the sum of the carbon atoms in $R_1$, $R_2$ and $R_3$ preferably being between ten and fifteen, and in all cases being at least ten, and (b) acid addition salts thereof. The group $R_3$ is preferably but not necessarily an omega-substituted hydroxyalkyl group.

These novel compounds of Formula I have valuable pharmacological properties, especially as inhibitors of dental plaque as further elucidated hereinafter, which makes them useful not only as anti-plaque, but also as anticaries and antiperiodontitis, products.

OBJECTS

It is an object of the present invention to provide novel alkyl 1-(hydroxyalkyl)piperidines and acid addition salts, thereof, which are useful in the chemical inhibition of dental plaque and resulting problems or ailments, a process for producing the same, orally-acceptable compositions thereof, intermediates therefor, and a method of treating therewith. Additional objects will become apparent hereinafter, and still others will be obvious to one skilled in the art.

BRIEF DESCRIPTION OF THE DRAWINGS

In the Drawings:

FIG. 1 is a schematic drawing of an artificial mouth, showing a tooth mounted for treatment or testing therein.

FIG. 2 is a view of three teeth tested in the artificial mouth for a period of fourteen (14) days while undergoing treatment for plaque inhibition, each tooth having been treated with a different substance.

FIG. 3 is a bar graph showing the relative increase of gingival fluid in the gingival pockets, indicative of the amount of gingival secretion, over a period of twenty-eight days while teeth were undergoing treatment with a representative compound of the invention and with a placebo.

PREPARATION

According to the present invention, the novel compounds of General Formula I are prepared according to any of the following reactions:

Reaction (a)

by reducing a mono- or di-oxo substituted piperidine of the General Formula II:

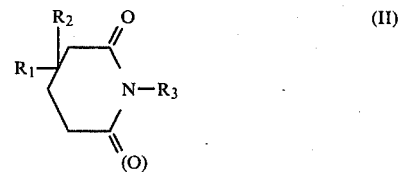
(II)

to a compound of Formula I. This reduction is preferably performed using lithium aluminum hydride (LAH) in diethylether or tetrahydrofuran according to conventional procedure for such type reaction. The reaction products are usually treated with water and sodium hydroxide and the solution of the piperidine derivative thus formed is distilled to give the desired product as the distillate.

The dioxoderivative II is prepared by treatment of the corresponding substituted glutaric acid

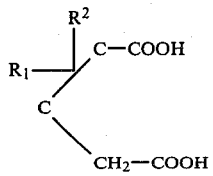 (X), its anhydride, or another derivative thereof, e.g., an ester thereof, with a compound of the Formula VII:

NH$_2$.R$_3$ (VII)

The reaction is generally performed by heating a mixture of the compounds at 100°–250° Centigrade in an autoclave for ten to twenty hours without solvent. The yield is better than seventy-five percent. The designation "C" in Formula X represents CH$_2$ as hereinbefore defined, one of the CH$_2$ groups bearing the gem-substituents

The monooxoderivative

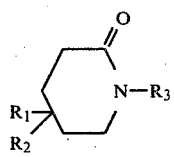 (XI) (II')

is synthesized from a substituted omega-halogenvaleric acid

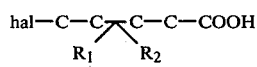 (XII)

wherein "C" once again stands for CH$_2$, one of which C atoms bears the gem-substituents as aforesaid. The ring is closed in the same manner as given for production of X, under similar conditions.

Reaction (b)

by alkylating a piperidine derivative having the Formula III:

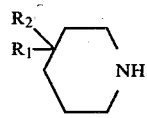 (III)

with an alkylating agent of the Formula IV:

R$_3$X (IV)

wherein X is halogen or an organic sulfonic ester or, together with an OH-group present in the alkylating agent IV, represents a reactive oxide.

Reaction b (1)

Synthesis of the piperidine III is performed by ring closure of the corresponding compound of Formula X or XII with NH$_3$ or NH$_2$CONH$_2$ in the manner described under (a). The mono- or dioxocompounds are reduced with LAH as described in (a) to a compound of Formula III. The piperidine III is reacted with, e.g., a halogenalkanol, an alkylene oxide, or an organic sulfonic ester, in a suitable solvent such as benzene or xylene. When using halogenalkanols or an organic sulfonic ester, the reaction is performed either with an excess of the piperidine or in the presence of another acid binding agent, such as a tertiary amine, e.g., triethylamine, potassium carbonate, or a similar acid binding agent, and preferably at an increased temperature, e.g., 74°–150° Centigrade in an autoclave. The above-described synthesis is suitable and can be carried out for all substituted piperidines having the General Formula I.

Reaction b (2)

Monosubstituted piperidines of the Formula III':

 (III')

can be prepared by reduction of the pyridine derivative XIII:

 (XIII)

with, e.g., sodium in ethanol or, alternatively, catalytically with H$_2$, Rh (C) in 1-N HCl at fifty degrees Centigrade under three atmospheres of hydrogen pressure over a period of, e.g., seventy hours. The compound of Formula III' is alkylated to

 (I')

as described under b (1).

Reaction (c)

by reduction of the quaternary pyridine derivative V:

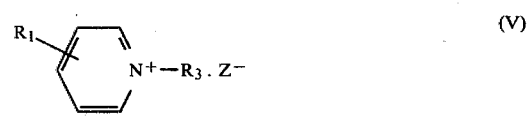 (V)

wherein Z$^-$ is any anion, to

 (I')

wherein Z is e.g., halogen, especially Cl$^-$, with H$_2$ and PtO$_2$ at three atmospheres of hydrogen pressure in acetic acid medium at fifty degrees Centigrade over a period of twenty hours. The pyridine derivative is readily prepared from XIII and IV, in known manner for such type reactions.

Reaction (d)

by ring closure of a compound of the General Formula VI:

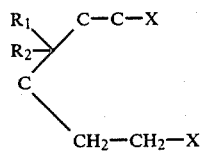   (VI)

with an aminoalkanol of the General Formula VII:

$H_2N.R_3$   (VII)

wherein $R_1$, $R_2$, $R_3$ have the meanings hereinbefore assigned, X is halogen or an organic sulfonic ester group, and wherein "C" once again represents $CH_2$, one of the $CH_2$ groups in the Formula VI being substituted with

Reaction d (1)

by reduction of an ester of the substituted glutaric acid of Formula X to the diol of Formula XV:

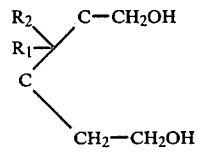   (XV)

This reduction is performed with LAH in the usual manner. The hydroxyl groups are halogenated with, e.g., $SOCl_2$ to produce:

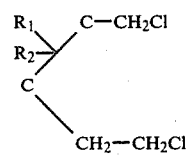   (VI)

and the ring then closed with $H_2NR_3$ (Formula VII) at 120°–170° Centigrade in an autoclave. The reaction is performed in the presence of an acid-binding agent, e.g., potassium carbonate or a tertiary amine. "C" again represents $CH_2$ as hereinbefore defined and explained.

Reaction d (2)

by treatment of a substituted tetrahydropyran of Formula VIII:

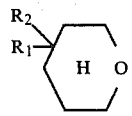   (VIII)

with a compound of Formula VII. The pyran of Formula VIII can be prepared by heating a compound of Formula XV with sulfuric acid and distillation of the product. It is transformed with a compound of formula VII to a compound of Formula I at 200°–300° Centigrade in an autoclave.

Reaction (e)

by use of a piperidino compound having the Formula IX:

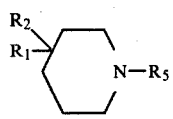   (IX)

wherein $R_5$ is alkyl, straight or branched, and contains a group which is transformable to OH or $CH_2OH$.

Reaction e (1)

$R_5$ contains halogen, $NH_2$, -OAc, O-alkyl, O-$CH_2C_6H_5$.

Reaction e (2)

$R_5$ contains -COOEt, -CN, CHO, or is $-CO(CH_2)_n COOEt$, wherein n is, 0 to 8.

The compound IX is synthesized as described in (b). Amine groups in the side chain $R_5$ are protected by acylation, usually acetylation. Halogen is transformed to acetoxy by treatment with silver acetate in acetic acid at 100° Centigrade. Acetamine groups (-NHAc) are hydrolyzed to amine ($NH_2$) and the amine ($NH_2$) group is transformed to hydroxyl by treatment with $NaNO_2$ in acid solution. Acetate groups are hydrolyzed to hydroxyl with alkali. $CH_2C_6H_5$ is removed by reduction in ordinary manner for reestablishment of a hydroxyl group. Remaining groups are converted to hydroxyl in the usual manner.

The final product I may be obtained as the free base or dissolved in a suitable solvent, e.g., diethylether, from which it can be precipitated as a salt, preferably with a pharmaceutically acceptable acid, e.g., hydrochloric or hydrobromic acid, oxalic acid, maleic acid, citric acid, tartaric acid, or the like, alcoholic hydrochloric acid being preferred for convenience. An acid salt, even if not pharmaceutically acceptable, is still useful, as it can readily be converted into another salt which is pharmaceutically acceptable in known manner, e.g., by alkalization and reacidification with a different acid, if desired.

DETAILED DESCRIPTION OF THE INVENTION

The following Preparations and Examples are given by way of illustration only.

EXAMPLE 1

4-n-octyl-1-(3-hydroxypropyl)piperidine hydrochloride

Twenty-eight (28) grams of 2,6-dioxo 4-n-octyl-1-(3-hydroxypropyl)piperidine is added with stirring to 15 grams of LAH suspension in one liter of dry diethyl ether and the reaction mixture is refluxed for 2.5 hours and decomposed by slow addition of water. The precipitate is filtered off. The ether solution is dried, evaporated, and the residue is distilled to give the product boiling at 130°–132° C./0.01 mm Hg. Yield 22 grams. The free base is dissolved in ether and the hydrochloride precipitated with alcoholic hydrochloric acid. After recrystallization, the melting point of the hydrochloride is 153°–157° C.

EXAMPLES 2-21

Proceeding according to method (a) generally as described in Example 1, from the appropriate starting materials, further compounds according to the invention as set forth in Table 1 were prepared.

EXAMPLES 22-24

The compounds in Table 2 were prepared from the selected starting materials as described in Example 1.

EXAMPLES 25-44

Proceeding according to method (b), as described in Example 25 and method (e2), as described in Example 39, the compounds set forth in Table 3 were prepared.

EXAMPLE 25

4-n-hexyl-1-(5-hydroxypentyl)piperidine hydrochloride

Seventeen (17) grams of 4-n-hexylpiperidine, 13 grams of 5-chloropentanol and 11 grams of triethylamine were dissolved in 100 ml. of toluene. The solution is heated in an autoclave for twelve hours at 120°–140° Centigrade. The solution is stirred with 200 ml. of 5-N NaOH. The organic phase is separated, dried, the solvent evaporated and the base distilled at 130°–135° Centigrade/0.01 mm Hg. The yield is 17.5 grams. The hydrochloride is obtained in the usual manner, according to Example 1, and melts at 142°–145° Centigrade.

EXAMPLE 39

4-n-decyl-1-(4-hydroxybutyl)piperidine hydrochloride

To a mixture of 23 grams of 4-n-decylpiperidine and 13 grams of triethylamine in 100 ml. of benzene, is slowly added with agitation 17 grams of succinic acid ethylesterchloride. The reaction is violent and is allowed to go to completion after the addition. The precipitate is filtered off. The solution is added to a mixture of 10 grams LAH in 500 ml. of dry diethylether. The reaction mixture is refluxed for three hours. The reaction complex is decomposed by slow addition of water. The precipitate is filtered off. The ether-benzene solution is dried and evaporated. The residue is distilled to give the desired product at 145°–147° Centigrade/0.01 mm. Hg. The yield is 28 grams (97%). The hydrochloride is precipitated as in Example 1. After recrystallization, the melting point of the hydrochloride is 152°–154° Centigrade.

TABLE 1

$R_1$—(piperidine ring)—$N$—$R_3$ . HCl Synthesized by Reaction (a)

| Comp No. | $R_1$ | $R_3$ | M.p. of the hydrochloride °C. | Plaque inhibiting effect |
|---|---|---|---|---|
| 1 | n-$C_8H_{17}$ | $CH_2CH_2CH_2OH$ | 153–157 | +++ |
| 2 | n-$C_7H_{15}$ | $CH_2CH_2CH_2OH$ | 152–153 | (+) |
| 3 | n-$C_{10}H_{21}$ | $CH_2CH_2CH_2OH$ | 155–157 | ++ |
| 4 | n-$C_9H_{19}$ | $CH_2CH_2CH_2OH$ | 158–159 | +++ |
| 5 | n-$C_9H_{19}$ | $CH_2CH_2OH$ | 122–123 | +++ |
| 6 | n-$C_8H_{17}$ | $CH_2CH_2OH$ | 131–132 | + |
| 7 | n-$C_9H_{19}$ | $CH_2CH_2CH_2CH_2OH$ | 148–150 | +++ |
| 8 | n-$C_8H_{17}$ | $CH_2CH_2CH_2CH_2OH$ | 148–149 | +++ |
| 9 | n-$C_7H_{15}$ | $CH_2CH_2CH_2CH_2OH$ | 145–147 | ++ |
| 10 | n-$C_8H_{17}$ | $CH_2CH_2CH_2CH_2CH_2OH$ | 148–149 | +++ |
| 11 | n-$C_7H_{15}$ | $CH_2CH_2CH_2CH_2CH_2OH$ | 133–136 | +++ |
| 12 | n-$C_7H_{15}$ | $CH_2CH_2CH_2CH_2CH_2CH_2OH$ | 148–151 | +++ |
| 13 | $(CH_3)_2CH(CH_2)_5$ | $CH_2CH_2CH_2OH$ | 157–158 | +++ |
| 14 | $C_2H_5(C_4H_9)CHCH_2$ | $CH_2CH_2CH_2OH$ | 172–173 | + |
| 15 | n-$C_9H_{19}$ | —$(CH_2)_5OH$ | 143–144 | ++ |
| 16 | n-$C_9H_{19}$ | —$(CH_2)_6OH$ | 155–156 | ++ |
| 17 | n-$C_9H_{19}$ | $CH_2CH(OH)CH_3$ | 103–105 | + |
| 18 | $(CH_3)_2CH(CH_2)_5$ | $(CH_2)_4OH$ | 124–125 | + |
| 19 | n-$C_8H_{17}$ | $(CH_2)_6OH$ | 163–164 | + |
| 20 | n-$C_{10}H_{21}$ | $(CH_2)_2OH$ | 126–128 | + |
| 21 | n-$C_{10}H_{21}$ | $(CH_2)_5OH$ | 140–144 | +++ |

TABLE 2

$R_1, R_2$ substituted piperidine $N-R_3 \cdot$ HCl Synthesized by Reaction (a)

| Comp. No. | $R_1$ | $R_2$ | $R_3$ | M.p. of the hydrochloride °C. | Plaque inhibiting effect |
|---|---|---|---|---|---|
| 22 | n-$C_7H_{15}$ | $CH_3$ | $CH_2CH_2CH_2OH$ | 214–216 | +++ |
| 23 | n-$C_7H_{15}$ | $CH_3$ | $CH_2CH_2CH_2CH_2OH$ | 182–184 | ++ |
| 24 | n-$C_8H_{17}$ | $CH_3$ | $CH_2CH_2CH_2OH$ | 212–213 | +++ |

TABLE 3

$R_1, R_2$ substituted piperidine (positions 2,3,4) $N-R_3$ Synthesized by Reaction (b) [39 according to Reaction (e)]

| Com No. | $R_1$ | $R_2$ | $R_3$ | M.p. of the hydrochloride °C. | Plaque inhibiting effect |
|---|---|---|---|---|---|
| 25 | 4-n-$C_6H_{13}$ | 4-H | $(CH_2)_5OH$ | 142–145 | (+) |
| 26 | 4-n-$C_{10}H_{21}$ | 4-H | $(CH_2)_3OH$ | 155–157 | ++ |
| 27 | 4-n-$C_9H_{19}$ | 4-H | $(CH_2)_3OH$ | 158–159 | +++ |
| 28 | 4-n-$C_9H_{19}$ | 4-H | $(CH_2)_4OH$ | 148–150 | +++ |
| 29 | 4-n-$C_8H_{17}$ | 4-H | $CH_2-CH(CH_3)-OH$ | 100–102 | ++ |
| 30 =22 | 4-n-$C_7H_{15}$ | 4-$CH_3$ | $CH_2CH_2CH_2OH$ | 213–215 | +++ |
| 31 | 3-H | 3-n-$C_9H_{19}$ | $CH_2CH_2CH_2OH$ | 120–127 | +++ |
| 32 | 3-H | 3-n-$C_9H_9$ | $CH_2CH_2OH$ | 119–122 | +++ |
| 33 | 4-$(C_2H_5)(C_3H_7-CH(CH_3))CH-CH_2$ | 4-H | $CH_2CH_2CH_2OH$ | 157–158 | +++ |
| 34 =24 | 4-n-$C_8H_{17}$ | 4-$CH_3$ | $CH_2CH_2CH_2OH$ | 211–212 | +++ |
| 35 | 4-$(n-C_3H_7)_2CHCH_2$ | 4-H | $CH_2CH_2CH_2OH$ | 171–172 | +++ |
| 36 | 4-$(n-C_3H_7)_2CHCH_2$ | 4-H | $CH_2CH_2OH$ | 146–147 | +++ |
| 37 | 2-n-$C_9H_{19}$ | 2-H | $CH_2CH_2CH_2OH$ | 76–79 | +++ |
| 38 | 4-n-$C_8H_{17}$ | 4-H | $CH(C_2H_5)-CH_2OH$ | 105–106 | + |
| 39 | 4-n-$C_{10}H_{21}$ | 4-H | $(CH_2)_4OH$ | 152–154 | ++ |
| 40 =15 | 4-n-$C_9H_{19}$ | 4-H | $(CH_2)_5OH$ | 144–145 | ++ |
| 41 | 4-n-$C_6H_{13}$ | 4-H | $(CH_2)_5OH$ | 142–145 | (+) |
| 42 | 4-n-$C_6H_{13}$ | 4-H | $(CH_2)_6OH$ | 160–162 | + |
| 43 | 4-n-$C_6H_{13}$ | 4-H | $(CH_2)_7OH$ | 141–144 | (+) |
| 44 | 4-n-$C_5H_{11}$ | 4-H | $(CH_2)_6OH$ | 147–149 | (+) |
| 43 | 4-n-$C_3H_7$ | 4-H | $(CH_2)_{10}OH$ | 169–172 | (+) |
| 44 | 4-n-$C_{11}H_{23}$ | 4-H | $(CH_2)_4OH$ | 147–150 | (+) |

Note:
The parentheses, when present in the last column of the Tables, signify that the activity is very weak.

Note: The parentheses, when present in the last column of the Tables, signify that the activity is very weak.

Moreover, in addition to the substituents $R_1$ $R_2$ shown in Tables 1–3, the same and/or different $R_1$ $R_2$ substituents may be present in different ring positions, e.g., in a different one of the 2, 3, or 4 positions or as a second ($R_2$) substituent at a particular carbon atom of the piperidine ring in addition to the $R_1$ substituent already present therein, and the hydroxy group may be primary, secondary, or tertiary and present at different or varying carbon atoms of the $R_3$ hydroxyalkyl substituent, such as at the 2, 3, 4, or 5 carbon atom thereof, depending only upon a judicious selection of the starting materials and the ring positions and substituents present in the starting compounds employed in the preceding preparations, as will be apparent and within the ability of one skilled in the art, including various acid addition salts thereof, e.g., the hydrochlorides, hydrobromides, oxalates, citrates, or tartrates of such compounds.

PHARMACOLOGY

Representative compounds of the present invention have been subjected to a series of in vitro and in vivo tests in which the new compounds were compared with controls. The test results have shown the compounds of the invention to be extremely valuable for the aforesaid purposes, as indicated in the "Plaque-inhibiting Effect" column of the foregoing Tables 1, 2, and 3.

By way of further explanation, the oral diseases periodontitis and dental caries in man or lower animals appear to be the result of complex biological interactions of various organisms of which dental plaque is composed. Chronic periodontitis, perhaps the most common cause of tooth loss, is an inflammatory process of the supporting tissues of the teeth and about as prevalent as dental caries.

The development of such tooth diseases has a common origin or cause, viz., dental plaque. The dental plaque is a deposit upon the surface of a tooth which contains, for example, food debris which acts as a medium for a variable bacterial flora. It leads to a special structure of a harder water-insoluble plaque, followed by an onset of both caries and inflammatory periodontal disease in this region.

In the field of oral and dental hygiene, a large variety of preparations are already employed as cleansing and hygienic agents for the oral cavity. They may be used in tooth pastes, tablets, and a myriad of other forms. A wide variety of chemical and biological agents have also been suggested for retarding dental plaque after it is once formed, or to protect the teeth against the resulting diseases. However, the mechanical removal of the dental plaque is, up to now, still the most effective method. The chemical approach to plaque inhibition has, on the other hand, involved different groups of compounds, antibiotics, chemotherapeutics and disinfectants, fluoro compounds, organic phosphatases, chelate-forming compounds, emulgators, and the like. Some examples are penicillin (antibiotics), chlorohexidine and 8-hydroxyquinoline (disinfectants), ethylenediaminetetraacetate (chelate-forming), and sodium fluoride (strengthening of the tooth enamel).

Some of these compounds have exhibited insignificant effects. Others, such as antiseptics and antibiotics, are likely to produce cures worse than the diseases themselves, and still others have a contested toxicity, e.g., the fluorine compounds. Sodium fluoride, for example, may not be used as an antiplaque compound, but only under close supervision as an enamel-reinforcing compound.

It seems clear that the plaque formation is of a very complicated nature and, for its chemical removal or inhibition, it is necessary to employ compounds with a special chemical structure without pronounced antibacterial effect and with very low toxicity.

The compounds according to the present invention have been submitted to intensive in vitro and in vivo tests and compared with reference substances which have been or are clinically used, and the results were found to be extremely favorable.

In vitro tests have been performed in an artificial mouth (FIG. 1).

Artificial mouth

The plaque-inhibiting effect of the compounds of the invention has been studied in a so-called artificial mouth originally described by Pigman et al. (J. dent. Res. 31, 627, 1952), but later modified (Naylor et al., "Dental Plaque", 1969).

The apparatus (A) (see FIG. 1) is made of glass and provided with a jacket and several connections. One or two extracted human teeth (B) mounted on a glass rod are introduced from one side and fixed. By peristaltic pumps (not shown), a slow-moving flow of substrate, bacteria (Streptococcus mutans) and sterile pooled saliva (all designated C) is supplied, and this substrate is directed so as to drop down on the fixed tooth surface. The space, within the apparatus in which the teeth have been placed, is subjected to a slight overpressure of a mixture of carbon acid and nitrogen, designated D. The temperature inside the test vessel is maintained constant at 35° C. by means of thermostated water circulating in the jacket. Many such apparatuses can be connected in series, as indicated by the arrow in FIG. 1.

After three to four days, teeth mounted and treated in this manner develop plaques on the surface thereof. These plaques consist of saliva components, cellular fragments and bacteria.

By removing the mounted teeth, at certain intervals from the beginning of the test, and treating them by contacting them with different substances, it can be investigated whether the plaque formation is inhibited in its development, i.e., the plaque-inhibiting effect of a substance can be determined.

Tests with our new substances have shown that they exert a clear plaque-inhibiting effect, much better than chlorohexidine or sodium fluoride. Chlorohexidine, besides its antiseptic activity, as already stated, has other undesired side effects such as discoloration of the teeth and development of bacterial resistance by continuous use. The test results have shown that, even after fourteen days, no plaque has been formed on teeth contacted with a compound of the present invention. This is obvious from an inspection of FIG. 2, which shows the results of a treatment period of fourteen days in the artificial mouth, the number of contacts of the teeth with the various three treatment agents being twice a day, thirty seconds each time.

Tests in vivo

For tests in vivo of the plaque-inhibiting effect, dogs have proved to be suitable experimental animals (Egelberg: Odont Revy 16, 31–41, 1965).

Such in vivo tests have been performed by giving the dogs hard food and several tooth-cleanings during a period of fourteen days, as a result of which the dogs have obtained a very good tooth status, i.e., clean teeth without caries, as well as gingival pockets and other membranes of the oral cavity being clinically without objection.

After these weeks of preliminary treatment, the real test was begun. The dogs were now given soft food and the tooth-cleaning was eliminated, thereby creating favorable conditions for plaque formation and, later on, tooth decay.

By painting the teeth of the same dogs at one time with a compound of the invention, e.g., Compound 1, and at another time with physiological saline, it was possible to observe to what extent a plaque inhibition occurred. Another way to record plaque formation and its inhibition is to estimate, quantitatively, the increase of gingival fluid in the gingival pockets, which means that the secretion of gingival fluid increases. (Attström et al.: J. periodont. Res., Preprint 1971). (See FIG. 3).

According to these criteria, we have studied the effect of our compounds, which have painted on the tooth surfaces twice a day over a four-week period. As a control on the same dogs, we have used physiological saline.

The visual as well as the quantitative estimations of the status of the teeth after treatment show that teeth treated with Compound 1 have a significantly lower formation of plaque than the control teeth (see FIGS. 2 and 3).

The novel compounds of the invention are preferably obtained and tested as their hydrochlorides or hydrofluorides. These salts are preferably also used in the oral preparations of the invention, although the free bases or other pharmacologically-acceptable salts may also be used. These salts can be prepared from the free bases according to conventional methods, e.g., using maleic, maleinic, or succinic acids, or the like, as previously set forth.

The preferred clinically-used formulations are dentifrices, paste or powder, mouth rinses, mouthspray, chewing gum, tablets, gargles, et cetera. In such preparations the compounds may advantageously be used in concentrations from 0.1 to 5% by weight. They may also be used together with other pharmacologically-active substances, e.g., sodium fluoride, 6-n-amyl-m-cresol, or 2,4-dichlorobenzylalcohol. Representative orally-acceptable oral and dental hygiene compositions are depicted in the following Examples 45–48.

EXAMPLE 45

| Tooth paste | |
|---|---|
| | Amounts per cent |
| Compound 1 | 1 |
| Dicalciumphosphate | 50 |
| Sorbitol | 6 |
| Glycerin | 18 |
| Na-carboxymethylcellulosa | 2 |
| Na-laurylsulphate | 1 |
| Na-saccharin | 0.1 |
| Peppermint oil | 0.9 |
| Water | up to 100 |

EXAMPLE 46

| Chewing Gum | |
|---|---|
| | Amounts per cent |
| Center | |
| Compound 1 | 3 |
| Fructose | 50 |
| Glycerin | 5 |
| Mannitol | 30 |
| Gum base | 2 |
| Carboxymethylcellulosa | 10 |
| Sodium cyclamate | 1 |
| Coating | |
| Carnauba wax with: | |
| Fructose | 9 |
| Gum arabic | 5 |
| Dextrin | 2 |
| Flavor | 2 |

The center compositions are mixtured at 50° C., compacted, and thereafter coated, all in usual manner.

EXAMPLE 47

| A chewable tablet | |
|---|---|
| | Grams |
| A mixture of: | |
| Compound 3 | 10 |
| Compound 4 | 10 |
| Sorbitol | 800 |
| Potato starch | 150 |
| 5% aqueous solution of gelatin | 30 |
| Peppermint oil | — |
| Na-cyclamate | 2 |

| -continued | |
|---|---|
| A chewable tablet | |
| | Grams |
| Na-saccharin | 1 | is tabletted to produce 1000 tablets with 1% of Compound 3 and 1% of Compound 4.

EXAMPLE 48

| Mouth Rinse Liquid | |
|---|---|
| | Amount by per cent |
| Compound 4 | 1 |
| Glycerin | 10 |
| Ethanol | 15 |
| Tween 80 (surfactant) | 0.1 |
| Na-cyclamate | 1.0 |
| Na-saccharin | 0.1 |
| Menthol flavor | 0.1 |
| Water | ad 100 |

Numerous other similar oral and dental hygiene formulations are available and will readily present themselves to one skilled in the art.

The novel compounds, as previously stated, are preferably used in the form of their pharmacologically-acceptable acid addition salts, e.g., their hydrochlorides, hydrobromides, or the like. The salt form is also the best form for orally-acceptable formulations. Innumerable other pharmacologically-acceptable acid addition salts can be prepared from the hydrochlorides via the free bases in conventional manner. For oral or dental hygiene use, the compounds may be employed as chewable or dissolvable tablets in which they are present together with usual orally-acceptable carriers, excipients, binders, and the like. For example, tablets may be prepared by conventionally by compounding one of the new compounds, preferably in the form of an acid addition salt thereof, with customary carriers and adjuvants, e.g., talc, magnesium stearate, starch, lactose, gelatin, gums, and the like.

In their most advantageous form, then, the compositions of the present invention will contain a non-toxic orally-acceptable carrier in addition to the active ingredient, i.e., a compound of Formula I. Exemplary carriers are: solids-lactose, magnesium stearate, calcium stearate, starch, terra alba, dicalcium phosphate, sucrose, talc, stearic acid, gelatin, agar, pectin, acacia, or the like; liquids-elixir, solution, or suspensions in water or the like. When sugars are employed, the inert or non-plaque-forming sugars are of course preferred. The active agents of the invention can be conveniently employed in the form of such compositions containing in their broadest aspects 0.01 to 67 percent, especially 0.04 to 12.15 percent, by weight of active ingredient, although 0.1 to 5% is definitely preferred. Such formulations and oral hygiene compositions are representatively illustrated in U.S. Pat. No. 3,751,561, with or without, but preferably without, the enzyme components as therein disclosed.

A wide variety of forms suitable for orally-acceptable usage and dosages may accordingly be employed. The active ingredient and orally-acceptable carrier may, for example, in its broader aspects take the form of a gum, granule, pill, tablet, lozenge, elixir, syrup, toothpaste, mouthwash, gargle, chewable tablet, or other liquid suspension or emulsion.

The method of using the compounds of the present invention comprises exposing a tooth or teeth, or the oral cavity in which the tooth or teeth are located, to the anti-dental plaque activity of a compound of Formula I, usually in the form of a non-toxic, pharmacologically-acceptable acid addition salt, and preferably admixed with an orally-acceptable carrier, for example, in the form of any of the above-mentioned compositions, or filled into a capsule, for the purpose of inhibiting formation of dental plaque on the tooth, and thereby also inhibiting complications which normally result therefrom, including dental caries and periodontitis. The compounds and their non-toxic salts, especially the hydrochlorides and hydrofluorides, may be advantageously employed in any desirable form and in amounts approximating those employed in the representative compositions of Example 45-48 hereof. Illustratively, they may be used in an amount of from about 0.1 to 100 milligrams per treatment, preferably from about 0.2 to 10 milligrams per treatment, depending upon the exact mode employed. The treatment is preferably given or undertaken a suitable number of times daily so that the daily treatment provides an effective amount of the active compound for the intended purpose, namely, inhibition of dental plaque and its resultant problems or complications as aforesaid, as already stated in the foregoing and as illustrated in the in vivo and in vitro tests reported.

In addition, the active ingredients of the present invention or compositions containing the same may either be administered together with or include other active materials and/or medicaments, e.g., buffering agents, antacids, flavors, anesthetics, antiseptics, surface-active agents, or the like. The compositions may take the form of impregnated dental floss, mouthwashes, gargles, candies, masticable candies, lozenges, tablets, toothpowders, sprays, toothpastes, dragees, creams, salves, ointments, denture cement or aids, breath purifiers, or other similar oral hygiene compositions.

The preceding formulations are representative and may be employed for incorporation of any of the pharmacologically-active compounds of the invention, but have been particularly designed to embody as active ingredient the particular compounds embodied therein, especially in the form of a pharmacologically-acceptable salt thereof, e.g., the tartrate, hydrochloride, hydrofluoride, hydrobromide, fumarate, or like pharmacologically-acceptable salt.

As will be apparent from the foregoing, the $R_1$ alkyl group, for best plaque inhibitory results, should have at least seven (7) carbon atoms. No compounds tested wherein $R_1$ had less than seven (7) carbon atoms gave total plaque inhibition. Such compounds are accordingly preferred. Further, branched-chain compounds are also preferred, especially the symmetrical branched-chain alkyl $R_1$ compounds as well as all other compounds which are given a three plus rating (total plaque inhibition) in the Tables herein. Moreover, a contact time of active ingredient with the tooth or teeth of thirty (30) seconds has been found adequate, and was the time employed in the artifical mouth tests. For practical use in animals and man, a contact time of ingredient or composition containing the same as short as ten (10) seconds is effective, as when used as a mouthwash, but of course longer contact times are of greater effectiveness and are preferred. Such contact times are conveniently thirty (30) seconds and may in fact be as long as ten to fifteen minutes or even longer, as when the active ingredient is presented in the form of a gum, although contact times of two (2) minutes and less are generally acceptable and more usual when the active ingredient is presented in the form of dentifrice, lozenge, chewable tablet, or the like. Concentrations of the active ingredient may broadly be 0.01 to 67 percent by weight, especially 0.04–12.5 percent, although for maximum effectiveness and operativeness a concentration of 0.1 to 5 percent by weight is definitely preferred. A concentration of active ingredient in compositions of the invention between 0.2 and 0.4 percent has been found very effective in plaque inhibition. As shown by the Examples herein, concentrations of one, two, and three percent by weight were extremely effective. Minimal plaque inhibitory concentrations were about 0.2 to about 0.4 percent on a weight per volume basis.

Especially preferred compounds of Formula I are those wherein $R_1$ is n-octyl, n-nonyl, or n-decyl, particularly those compounds wherein $R_2$ is hydrogen, and also those compounds wherein $R_3$ is 2-hydroxyethyl, 3-hydroxypropyl, 4-hydroxybutyl, 5-hydroxypentyl, and 6-hydroxyhexyl.

Various modifications in the compounds, compositions, and methods of the invention will be apparent to one skilled in the art and may be made without departing from the spirit or scope thereof, and it is therefore to be understood that the invention is to be limited only by the scope of the appended claims.

We claim:
1. An oral and dental hygiene composition suitable for use in the inhibition of dental plaque comprising (a) an alkyl 1-hydroxyalkylpiperidine having the Formula I,

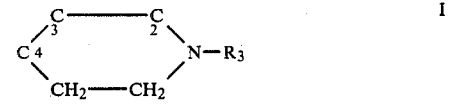

which is substituted in the 2,3, or 4 position with

wherein $R_1$ is an alkyl group, straight or branched, having at least seven carbon atoms, $R_2$ is hydrogen or an alkyl group, $R_1$ and $R_2$ together having 7–14 carbon atoms, and wherein $R_3$ is a hydroxyalkyl group of 2–6 carbon atoms, the sum of the carbon atoms in $R_1$, $R_2$, and $R_3$ being at least ten; "C" representing $CH_2$ except for the one carbon atom bearing the said $R_1 R_2$ substitution, or (b) an orally acceptable acid addition salt thereof, in an amount effective for said purpose, in association with an orally-acceptable carrier.

2. Composition of claim 1 wherein $R_3$ is omega-hydroxyalkyl.

3. Composition of claim 1 wherein the total number of carbon atoms in $R_1$, $R_2$, and $R_3$ is between ten and fifteen.

4. Composition of claim 1 wherein $R_1$ is selected from the group consisting n-octyl, n-nonyl, and n-decyl.

5. Composition of claim 1 wherein $R_3$ is selected from the group consisting of 2-hydroxyethyl, 3-hydroxypropyl, 4-hydroxybutyl, 5-hydroxypentyl, and 6-hydroxyhexyl.

6. Composition of claim 1 wherein $R_1$ is n-octyl and $R_3$ is 3-hydroxypropyl.

7. Composition of claim 1 wherein the active ingredient is a 4-n-octyl-1-(3-hydroxypropyl)piperidine acid addition salt.

8. Composition of claim 1 wherein $R_1$ and $R_2$ are both alkyl.

9. The composition of claim 1 wherein $R_1$ is a symmetrically branched octyl group.

10. The composition of claim 1 wherein $R_2$ is hydrogen or methyl.

11. The composition of claim 1 wherein $R_1$ is a n-nonyl and $R_3$ is 3-hydroxypropyl.

12. The composition of claim 1 wherein the active ingredient is 3-n-nonyl-1-(3-hydroxypropyl) piperidine acid addition salt.

13. The composition of claim 1 wherein the active ingredient is 3-n-nonyl-1-(3-hydroxypropyl) piperidine hydrochloride.

14. The composition of claim 1 wherein $R_1$ is 2,2-dipropylethyl and $R_3$ is 2-hydroxyethyl.

15. The composition of claim 1 wherein the active ingredient is 4-(2,2-dipropylethyl)-1-(2-hydroxyethyl) piperidine acid addition salt.

16. The composition of claim 1 wherein the active ingredient is 4-(2,2-dipropylethyl)-1-(2-hydroxyethyl) piperidine hydrochloride.

17. Method for the inhibition of dental plaque, comprising the step of contacting a tooth with (a) an alkyl 1-hydroxyalkylpiperidine having the Formula I,

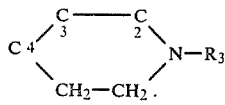

which is substituted in the 2, 3, or 4 position with

wherein $R_1$ is an alkyl group, straight or branched, having at least seven carbon atoms, $R_2$ is hydrogen or an alkyl group, $R_1$ and $R_2$ together having 7–14 carbon atoms, and wherein $R_3$ is a hydroxyalkyl group of 2–6 carbon atoms, the sum of the carbon atoms in $R_1$, $R_2$, and $R_3$ being at least ten; "C" representing $CH_2$ except for the one carbon atom bearing the said $R_1 R_2$ substitution, or (b) an orally acceptable acid addition salt thereof, in an amount effective for said purpose.

18. The method of claim 17, wherein $R_1$ is a symmetrically branched octyl group.

19. The method of claim 17 wherein $R_2$ is hydrogen or methyl.

20. The method of claim 17 wherein $R_1$ is n-nonyl and $R_3$ is 3-hydroxypropyl.

21. The method of claim 17 wherein the active ingredient is 3-n-nonyl-1-(3-hydroxypropyl) piperidine acid addition salt.

22. The method of claim 17 wherein the active ingredient is 3-n-nonyl-1-(3-hydroxypropyl) piperidine hydrochloride.

23. The method of claim 17 wherein $R_1$ is 2,2-dipropylethyl and $R_3$ is 2-hydroxyethyl.

24. The method of claim 17 wherein the active ingredient is 4-(2,2-dipropylethyl)-1-(2-hydroxyethyl) piperidine acid addition salt.

25. The method of claim 17 wherein the active ingredient is 4-(2,2-dipropylethyl)-1-(2-hydroxyethyl) piperidine hydrochloride.

26. The method of claim 17 wherein $R_3$ is omega-hydroxyalkyl.

27. The method of claim 17 wherein the total number of carbon atoms in $R_1$, $R_2$, and $R_3$ is between ten and fifteen.

28. The method in claim 17 wherein $R_1$ is selected from the group consisting of n-octyl, n-nonyl, and n-decyl.

29. The method of claim 17 wherein $R_3$ is selected from the group consisting of 2-hydroxyethyl, 3-hydroxypropyl, 4-hydroxybutyl, 5-hydroxypentyl, and 6-hydroxyhexyl.

30. The method of claim 17 where $R_1$ is n-octyl and $R_3$ is 3-hydroxypropyl.

31. The method of claim 17 wherein the active ingredient is a 4-n-octyl-1-(3-hydroxypropyl)piperidine acid addition salt.

32. The method of claim 17, wherein both $R_1$ and $R_2$ are alkyl.

33. A compound selected from the group consisting of (a) an alkyl 1-hydroxyalkyl piperidine having the formula B

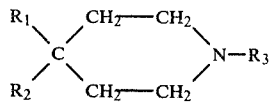

wherein $R_1$ is selected from the group consisting of 2,2-dipropylethyl and 2-ethyl-3-propylbutyl, $R_2$ is hydrogen, and $R_3$ is omega-hydroxyethyl or omega-hydroxypropyl, and (b) an orally-acceptable acid addition salt thereof.

34. The compound of claim 33 wherein $R_1$ is 2,2-dipropylethyl.

35. The compound of claim 33 wherein $R_1$ is 2-ethyl-3-propylbutyl.

36. The compound of claim 33 wherein $R_3$ is 2-hydroxyethyl.

37. The compound of claim 33 wherein $R_3$ is 3-hydroxypropyl.

38. The compound of claim 33 which is 4-(2,2-dipropylethyl)-1-(3-hydroxypropyl) piperidine acid addition salt.

39. The compound of claim 33 which is 4-(2,2-dipropylethyl)-1-(2-hydroxyethyl) piperidine acid addition salt.

40. The compound of claim 33 which is 4-(2,2-dipropylethyl)-1-(2-hydroxyethyl)piperidine hydrochloride.

41. The compound of claim 33 which is 4-(2-ethyl-3-propylbutyl)-1-(3-hydroxypropyl) piperidine acid addition salt.

42. The compound of claim 33 which is 4-(2,2-dipropylethyl)-1-(3-hydroxypropyl)piperidine hydrochloride.

43. The compound of claim 33 which is 4-(2-ethyl-3-propylbutyl)-1-(3-hydroxypropyl)piperidine hydrochloride.

* * * * *

UNITED STATES PATENT AND TRADEMARK OFFICE
CERTIFICATE OF CORRECTION

PATENT NO. : 4,235,875

DATED : November 25, 1980

INVENTOR(S) : Sven E. H. Hernestam, Lars O. Willard, Aina L. Abramo and Hans-Bertil Johansson It is certified that error appears in the above-identified patent and that said Letters Patent are hereby corrected as shown below:

Col. 4, line 12; "74°-150°" should read -- 75°-150° --

Col. 6, lines 32 & 33; "-CO(CH$_2$)$_n$COOEt," is incorrectly hyphenated - if formula is hyphenated it should read -- -CO(CH$_2$)$_n$-COOEt, --

Col. 7, lines 29 & 30; "triethylamine" incorrectly hyphenated should read -- triethyl-amine --

Col. 9, lines 63 & 64; delete "Note: The parentheses, when present in the last column of the Tables, signify that the activity is very weak."

Col. 12, line 39; "Odont Revy" should read -- Odont. Revy --

Col. 12, line 62; "have painted" should read -- have been painted --

Col. 15, line 17; "Example" should read -- Examples --

Col. 15, line 38; "cement" should read -- cements --

Col. 15, lines 62 & 63; "of ingredient" should read -- of active ingredient --

Col. 16, line 64; "consisting n-octyl," should read -- consisting of n-octyl, --

Col. 16, lines 67 & 68; "6-hydroxyhexyl." incorrectly hyphenated should read -- 6-hydroxy-hexyl. --

Col. 18, lines 16 & 17; "3-hydroxypropyl," incorrectly hyphenated should read -- 3-hydroxy-propyl, --

Signed and Sealed this

Tenth Day of March 1981

[SEAL]

Attest:

RENE D. TEGTMEYER

Attesting Officer     Acting Commissioner of Patents and Trademarks